(12) United States Patent
Azemi et al.

(10) Patent No.: US 8,173,845 B2
(45) Date of Patent: May 8, 2012

(54) PROCESS FOR PRODUCING 3-METHYLTHIOPROPANAL

(75) Inventors: Takushi Azemi, Ehime (JP); Michiaki Maruyama, Niigata (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 232 days.

(21) Appl. No.: 12/755,003

(22) Filed: Apr. 6, 2010

(65) Prior Publication Data

US 2010/0256419 A1  Oct. 7, 2010

(30) Foreign Application Priority Data

Apr. 6, 2009 (JP) .................. 2009-091872

(51) Int. Cl.
*C07C 319/18* (2006.01)
(52) U.S. Cl. ........................................ 568/41
(58) Field of Classification Search ........... 568/41
See application file for complete search history.

(56) References Cited

U.S. PATENT DOCUMENTS

| 2004/0063650 A1 | 4/2004 | Shiozaki et al. |
| 2006/0030739 A1 | 2/2006 | Dubner et al. |

FOREIGN PATENT DOCUMENTS

| JP | 56-074114 A | 6/1981 |
| JP | 06-145100 A | 5/1994 |
| JP | 09-501145 A | 2/1997 |
| JP | 11-511119 A | 9/1999 |
| JP | 2004-115461 A | 4/2004 |
| WO | 9429254 A1 | 12/1994 |
| WO | 9640631 A1 | 12/1996 |

OTHER PUBLICATIONS

EP Search Report issued on Jul. 28, 2010 in EP Application No. 10 15 9111.
HU Search Report and Written Opinion dated Jun. 16, 2011 in application 201002400-8.

*Primary Examiner* — Sikarl Witherspoon
(74) *Attorney, Agent, or Firm* — Panitch Schwarze Belisario & Nadel LLP

(57) ABSTRACT

A process is provided capable of producing 3-methylthiopropanal with subgeneration of high-boiling impurities being favorably inhibited. The process for producing 3-methylthiopropanal, includes reacting acrolein with methylmercaptan in the presence of a triallylamine compound represented by the formula (I):

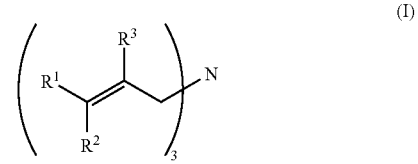

(I)

wherein each of $R^1$ to $R^3$ represents a hydrogen atom or an alkyl group having 1 to 4 carbon atoms. The reaction of acrolein with methylmercaptan is preferably performed further in the presence of an organic acid. The triallylamine compound represented by the formula (I) is preferably used in an amount of from 0.01 to 1.0 mol based on one mole of the organic acid and in an amount of from 0.1 to 2.0 mmoles based on one mole of methylmercaptan.

5 Claims, No Drawings

PROCESS FOR PRODUCING 3-METHYLTHIOPROPANAL

CROSS-REFERENCE TO RELATED APPLICATIONS

The present application is filed, claiming the Paris Convention priority of Japanese Patent Application No. 2009-91872 (filed on Apr. 6, 2009), the entire content of which is incorporated herein by reference.

BACKGROUND OF THE INVENTION

The present invention relates to a process for producing 3-methylthiopropanal by reacting acrolein with methylmercaptan. 3-methylthiopropanal is useful, for example, as a material for methionine.

It is widely known as a process for producing 3-methylthiopropanal by reacting acrolein with methylmercaptan that the reaction is performed in the presence of pyridines (cf. JP-A-2004-115461, JP-A-11-511119, JP-A-9-501145, etc.).

BRIEF SUMMARY OF THE INVENTION

However, the above-mentioned conventional process is not necessarily satisfactory in view of subgeneration of high-boiling impurities. Thus, an object of the present invention is to provide a process for producing 3-methylthiopropanal with subgeneration of high-boiling impurities being favorably inhibited.

The present inventors have intensively studied and found a process which can achieve the above object. Thus, the present invention has been completed.

The present invention is intended to provide the following:

<1> A process for producing 3-methylthiopropanal, comprising reacting acrolein with methylmercaptan in the presence of a compound represented by the formula (I):

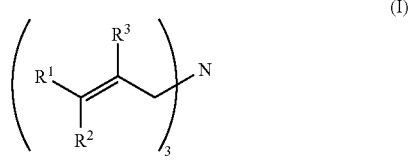

wherein each of $R^1$ to $R^3$ represents a hydrogen atom or an alkyl group having 1 to 4 carbon atoms.

<2> The process according to the above item <1>, wherein the reaction of acrolein with methylmercaptan is performed further in the presence of an organic acid.

<3> The process according to the above item <2>, wherein the compound represented by the formula (I) is used in an amount of from 0.01 to 1.0 mol based on one mole of the organic acid.

<4> The process according to any one of the above items <1> to <3>, wherein the compound represented by the formula (I) is used in an amount of from 0.1 to 2.0 mmoles based on one mole of methylmercaptan.

<5> The process according to any one of the above items <1> to <4>, wherein the reaction of acrolein with methylmercaptan is performed while each of acrolein, methylmercaptan, and a mixture of the compound represented by the formula (I) and the organic acid is fed into the reaction system.

According to the present invention, 3-methylthiopropanal can be produced with subgeneration of high-boiling impurities being favorably inhibited.

DETAILED DESCRIPTION OF THE INVENTION

In the present invention, a compound (hereinafter optionally referred to as a triallylamine (I)) represented by the formula (I):

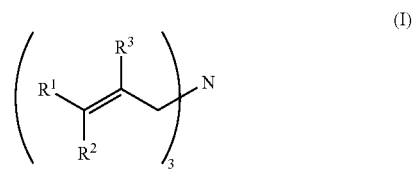

wherein each of $R^1$ to $R^3$ represents a hydrogen atom or an alkyl group having 1 to 4 carbon atoms is used. Subgeneration of high-boiling impurities can be favorably inhibited by using the triallylamine (I) as a catalyst. In the formula (I), examples of the alkyl group having 1 to 4 carbon atoms include a methyl group, an ethyl group, a n-propyl group, an iso-propyl group, a n-butyl group, a sec-butyl group, and a tert-butyl group. Examples of a triallylamine (I) include triallylamine, i.e. a compound of the formula (I) wherein all of $R^1$ to $R^3$ represent a hydrogen atom, tri(2-butenyl)amine, tri(3-methyl-2-butenyl)amine, tri(2-pentenyl)amine, and tri(2-hexenyl)amine. Two or more thereof may optionally be used. Among them, triallylamine is preferable.

In the present invention, subgeneration of highboiling impurities can be more favorably inhibited by using an organic acid in addition to the triallylamine (I). Examples of the organic acid include, for example, carboxylic acids; aliphatic monocarboxylic acids, such as formic acid, acetic acid, propionic acid, octanoic acid, acrylic acid, trichloroacetic acid, and trifluoroacetic acid; aromatic monocarboxylic acids, such as phenylacetic acid, benzoic acid, cinnamic acid, furoic acid, and thiophenecarboxylic acid; aromatic polycarboxylic acids, such as phthalic acid; sulfate monoesters; and sulfonic acid. Among them, carboxylic acids are preferable and acetic acid is more preferable.

Conventionally, methylmercaptan is used nearly in an equimolar amount with acrolein. In view of odor reduction of resultant 3-methylthiopropanal, it is preferable that acrolein is in slight excess and thus it is preferred to use from 0.95 to 0.99 mol of methylmercaptan based on one mole of acrolein.

The amount of a triallylamine (I) used may be appropriately selected and is preferably from 0.1 to 2.0 mmoles based on one mole of methylmercaptan. In the case of coexistence of an organic acid, the amount is preferably from 0.01 to 1.0 mol and more preferably from 0.3 to 0.7 mol based on one mole of the organic acid.

A mixing procedure for acrolein, methylmercaptan, and a triallylamine (I) is not specifically limited, and examples thereof may include a method in which a mixture of acrolein and a triallylamine (I) is admixed with methylmercaptan, a method in which a mixture of methylmercaptan and a triallylamine (I) is admixed with acrolein, and a method in which each of acrolein, methylmercaptan, and a triallylamine (I) is fed respectively into a reaction system to admix with each other. Among them, a method in which each of acrolein, methylmercaptan, and a triallylamine (I) is fed respectively into a reaction system is preferred. In the case of using an organic acid, it is preferred that an organic acid is premixed with a triallylamine (I) and the mixture is admixed with acrolein and methylmercaptan, and it is particularly preferred that acrolein, methylmercaptan, a mixture of triallylamine (I) and an organic acid is fed respectively into a reaction system.

The reaction system to be applied may be batch-wise or continuous, and a continuous system is preferably applied in view of productivity. The reaction temperature to be applied is usually from −10 to 100° C., and preferably from 0 to 80° C. The reaction time to be applied is usually from 10 minutes to 24 hours. The reaction may be conducted either under reduced pressure, under ordinary pressure, or under pressure. In addition, further components, such as a solvent inactive against the reaction, may be optionally fed in the reaction mentioned above.

Any known methods may be appropriately applied to the post-processing operation for the resultant reaction mixture containing 3-methylthiopropanal. The examples thereof include a method in which the reaction mixture is distilled and thus 3-methylthiopropanal is separated from the mixture and purified.

EXAMPLES

Examples of the present invention will now be described, but are not limited thereto.

Example 1

To a reactor equipped with a supply port for acrolein, a supply port for methylmercaptan and a supply port for a mixture of triallylamine and acetic acid were charged 122 g (2.00 moles) of acrolein (with purity of 92% by weight), 93.4 g (1.94 moles) of methylmercaptan, and 0.231 g (0.94 mmol of triallylamine and 1.70 mmoles of acetic acid) of a mixture of triallylamine and acetic acid in a molar ratio of 1:1.8, and a batchwise reaction was performed at a reaction temperature of from 0 to 30° C. for a reaction time of 30 minutes. The resultant reaction liquid was distilled under 20 torr at 70 to 120° C. to distil 3-methylthiopropanal away and the residual concentrate (i.e. a high-boiling oligomer) was weighed. The amount of the residual concentrate obtained was 0.3% by weight with respect to the reaction liquid.

Example 2

The same procedure as in Example 1 was carried out except that 0.0594 g (0.24 mmol of triallylamine and 0.44 mmol of acetic acid) of a mixture of triallylamine and acetic acid in a molar ratio of 1:1.8 was used. The amount of the residual concentrate (i.e. a high-boiling oligomer) in the reaction liquid was 0.3% by weight.

Example 3

The same procedure as in Example 1 was carried out except that the reaction was performed at a reaction temperature of from 40 to 70° C. The amount of the residual concentrate (i.e. a high-boiling oligomer) in the reaction liquid was 1.7% by weight.

Example 4

The same procedure as in Example 3 was carried out except that 0.119 g (0.48 mmol of triallylamine and 0.88 mmol of acetic acid) of a mixture of triallylamine and acetic acid in a molar ratio of 1:1.8 was used. The amount of the residual concentrate (i.e. a high-boiling oligomer) in the reaction liquid was 1.4% by weight.

Example 5

The same procedure as in Example 3 was carried out except that 1.02 g (1.38 mmoles of triallylamine and 13.8 mmoles of acetic acid) of a mixture of triallylamine and acetic acid in a molar ratio of 1:10 was used. The amount of the residual concentrate (i.e. a high-boiling oligomer) in the reaction liquid was 1.5% by weight.

Example 6

The same procedure as in Example 3 was carried out except that 0.314 g (1.38 mmoles of triallylamine and 2.07 mmoles of acetic acid) of a mixture of triallylamine and acetic acid in a molar ratio of 1:1.5 was used. The amount of the residual concentrate (i.e. a high-boiling oligomer) in the reaction liquid was 1.9% by weight.

Comparative Example 1

To a reactor equipped with a supply port for acrolein, a supply port for methylmercaptan and a supply port for a mixture of pyridine and acetic acid were charged 122 g (2.00 moles) of acrolein (with purity of 92% by weight), 93.4 g (1.94 moles) of methylmercaptan, and 0.938 g (1.38 mmoles of pyridine and 13.8 mmoles of acetic acid) of a mixture of pyridine and acetic acid in a molar ratio of 1:10, and a batchwise reaction was carried out at 0° C. on trial but no reaction took place.

Comparative Example 2

To a reactor equipped with a supply port for acrolein, a supply port for methylmercaptan and a supply port for a mixture of pyridine and acetic acid were charged 122 g (2.00 moles) of acrolein (with purity of 92% by weight), 93.4 g (1.94 moles) of methylmercaptan, and 0.938 g (1.38 mmoles of pyridine and 13.8 mmoles of acetic acid) of a mixture of pyridine and acetic acid in a molar ratio of 1:10, and a batchwise reaction was performed at a reaction temperature of from 40 to 70° C. for a reaction time of 30 minutes. The resultant reaction liquid was distilled under 20 torr at 70 to 120° C. to distil 3-methylthiopropanal away and the residual concentrate (i.e. a high-boiling oligomer) was weighed. The amount of the residual concentrate obtained was 2.6% by weight with respect to the reaction liquid.

Comparative Example 3

The same procedure as in Comparative Example 2 was carried out except that 0.911 g (1.06 mmoles of pyridine and 13.8 mmoles of acetic acid) of a mixture of pyridine and acetic acid in a molar ratio of 1:13.0 was used. The amount of the residual concentrate (i.e. a high-boiling oligomer) in the reaction liquid was 5.2% by weight.

Comparative Example 4

The same procedure as in Comparative Example 2 was carried out except that 0.233 g (1.38 mmoles of pyridine and 2.07 mmoles of acetic acid) of a mixture of pyridine and acetic acid in a molar ratio of 1:1.5 was used. The amount of the residual concentrate (i.e. a high-boiling oligomer) in the reaction liquid was 8.3% by weight.

Comparative Example 5

The same procedure as in Comparative Example 2 was carried out except that 1.08 g (1.38 moles of tributylamine and 13.8 moles of acetic acid) of a mixture of tributylamine and acetic acid in a molar ratio of 1:10 was used. The amount of the residual concentrate (i.e. a high-boiling oligomer) in the reaction liquid was 3.5% by weight.

Comparative Example 6

The same procedure as in Comparative Example 2 was carried out except that 0.455 g (1.38 mmoles of tributylamine and 3.31 mmoles of acetic acid) of a mixture of tributylamine and acetic acid in a molar ratio of 1:2.4 was used. The amount of the residual concentrate (i.e. a high-boiling oligomer) in the reaction liquid was 5.6% by weight.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A process for producing 3-methylthiopropanal, comprising reacting acrolein with methylmercaptan in the presence of a compound represented by the formula (I):

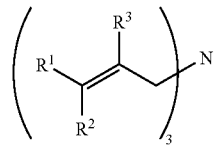

wherein each of $R^1$ to $R^3$ represents a hydrogen atom or an alkyl group having 1 to 4 carbon atoms.

2. The process according to claim 1, wherein the reaction of acrolein with methylmercaptan is performed further in the presence of an organic acid.

3. The process according to claim 2, wherein the compound represented by the formula (I) is used in an amount of from 0.01 to 1.0 mol based on one mole of the organic acid.

4. The process according to claim 1, wherein the compound represented by the formula (I) is used in an amount of from 0.1 to 2.0 mmoles based on one mole of methylmercaptan.

5. The process according to claim 2, wherein the reaction of acrolein with methylmercaptan is performed while each of acrolein, methylmercaptan, and a mixture of the compound represented by the formula (I) and the organic acid is fed into the reaction system.

\* \* \* \* \*